United States Patent [19]

Matsushita

[11] Patent Number: 5,087,730

[45] Date of Patent: Feb. 11, 1992

[54] METHOD FOR PRODUCING A PURIFIED ESTER

[75] Inventor: Yasunori Matsushita, Nagoya, Japan

[73] Assignee: Mitsubishi Kasei Vinyl Company, Tokyo, Japan

[21] Appl. No.: 538,529

[22] Filed: Jun. 15, 1990

[30] Foreign Application Priority Data

Jun. 27, 1989 [JP] Japan .................... 1-162569

[51] Int. Cl.$^5$ .............................. C07C 67/48
[52] U.S. Cl. ........................ 560/78; 560/99; 560/191; 560/204
[58] Field of Search ............... 560/78, 99, 191, 204

[56] References Cited

U.S. PATENT DOCUMENTS

| | | |
|---|---|---|
| 4,216,337 | 8/1980 | Baba et al. .................. 560/78 |
| 4,284,793 | 8/1981 | Sagara et al. ................ 560/78 |
| 4,304,925 | 12/1981 | Watanabe et al. ............ 560/78 |
| 4,506,091 | 3/1985 | Deardoff .................... 560/78 X |

FOREIGN PATENT DOCUMENTS 62-289236 12/1987 Japan .

*Primary Examiner*—José G. Dees
*Assistant Examiner*—Vera C. Clarke
*Attorney, Agent, or Firm*—Oblon, Spivak, McClelland, Maier & Neustadt

[57] ABSTRACT

A method for producing an ester, which comprises reacting an organic acid or its anhydride with an alcohol in the presence of a catalyst of an organometallic compound, wherein an esterification reaction product containing the catalyst, is treated with a polyhydric alcohol.

5 Claims, No Drawings

METHOD FOR PRODUCING A PURIFIED ESTER

The present invention relates to a method for producing an ester. More particularly, it relates to a method for producing a high quality ester useful as a plasticizer containing a minimum amount of impurities such as a catalyst, industrially advantageously by a simple operation.

As an advantageous method for producing an ester from an organic acid or its anhydride and an alcohol, a dehydration esterification method is widely known in which an organometallic compound such as tetraisopropyl titanate, tetrabutyl titanate or tetra-2-ethylhexyl titanate, is used as a catalyst. A wet method and a dry method are available to obtain a purified ester from the reaction product obtained by such a method.

As the wet method, a method is known wherein water is added to the reaction product, followed by heating to hydrolyze the catalyst, and then an alkali is added to neutralize any unreacted organic acid, then the obtained crude ester is thoroughly washed with water, followed by steam stripping or vacuum distillation, and then purification treatment is conducted by means of e.g. active carbon or activated clay (Japanese Unexamined Patent Publication No. 130937/1980). As the dry method, a method is known wherein the esterification reaction product is subjected to heat contact treatment with a solid alkali such as sodium carbonate in the absence of water, and subsequently, or simultaneously, it is subjected to contact treatment with an adsorbing agent such as activated clay (Japanese Unexamined Patent Publication No. 76517/1979).

The former wet method involves cumbersome steps and requires a long time for the purification treatment, and it has an additional disadvantage that the consumption of water for washing or heat energy is substantial. The latter drying method involves a solid-liquid reaction and thus requires a long time for the treatment, and by the high temperature heat treatment, the ester is likely to undergo a property change. Further, if the amount of the solid alkali used is at a level equivalent to the acid value of the ester, the removal of the catalyst will be difficult. On the other hand, if the solid alkali is used in a sufficient amount for the removal of the catalyst, then the costs and time for the recovery of alkali will be substantial, whereby the treatment will be costly.

It is an object of the present invention to produce a high quality ester containing a minimum amount of impurities such as the catalyst, industrially advantageously by a simple operation, without bringing about the above-mentioned drawbacks of the conventional methods.

The present inventors have conducted extensive studies to accomplish the above object. As a result, they have found that at the time of producing an ester by reacting an organic acid or its anhydride with an alcohol in the presence of a catalyst of an organometallic compound, if the esterification reaction product is treated with a polyhydric alcohol, the catalyst contained in the reaction product can readily be separated in the form of solid, whereby a high quality ester can readily and economically advantageously be obtained without requiring such a long time as required for the purification treatment by the conventional wet method and with less consumption of water for washing or heat energy. The present invention has been accomplished on the basis of this discovery.

Thus, the present invention provides a method for producing an ester, which comprises reacting an organic acid or its anhydride with an alcohol in the presence of a catalyst of an organometallic compound, wherein an esterification reaction product containing the catalyst, is treated with a polyhydric alcohol.

Now, the present invention will be described in detail with reference to the preferred embodiments.

In the present invention, the organic acid or its anhydride may be, for example, an aromatic polycarboxylic acid such as phthalic acid, phthalic anhydride, terephthalic acid, isophthalic acid, trimellitic acid, trimellitic anhydride or pyromellitic acid; an aliphatic saturated polycarboxylic acid such as adipic acid, sebacic acid or azelaic acid; an aliphatic unsaturated polycarboxylic acid such as maleic acid or fumaric acid; an aliphatic monocarboxylic acid such as oleic acid or stearic acid; or an aromatic monocarboxylic acid such as benzoic acid. The alcohol to be used for the production of an ester together with such an organic acid, may be, for example, an aliphatic saturated monohydric alcohol such as methyl alcohol, ethyl alcohol, n-propyl alcohol, isopropyl alcohol, n-butyl alcohol, isobutyl alcohol, secondary butyl alcohol, isoheptyl alcohol, n-octyl alcohol, 2-ethylhexyl alcohol, isooctyl alcohol, decanol, undecanol or tridecanol; an aliphatic polyhydric alcohol such as ethylene glycol, diethylene glycol or propylene glycol; or an aromatic monohydric alcohol such as benzyl alcohol. These alcohols may be used in combination as a mixture.

The catalyst of an organometallic compound in the present invention, may be an alkyl titanate showing catalytic activities at a temperature of at least 180° C. For example, tetrabutyl titanate, tetraisopropyl titanate or tetra-2-ethylhexyl titanate, may be employed.

The dehydration esterification reaction of the organic acid or its anhydride with the alcohol may be conducted in accordance with a well known method, for example, by mixing the starting material organic acid and the alcohol in a predetermined ratio, adding the catalyst of an organometallic compound thereto, and heating the mixture at a temperature of at least 180° C. for dehydration esterification.

The present invention is characterized in that the reaction product containing the catalyst obtained by the above esterification reaction, is treated with a polyhydric alcohol.

The polyhydric alcohol may be, for example, trimethylolpropane, trimethylolbutane, pentaerythritol, dipentaerythritol, sorbitol, sorbitan, a saccharide, cellulose, polyvinyl alcohol, or other aliphatic polyhydric alcohols which are commonly used as starting materials for esterification. These polyhydric alcohols may be used alone or in combination as a mixture of two or more different types. The amount of the polyhydric alcohol to be used, is preferably the amount represented by the following formula:

Amount of the polyhydric alcohol $= (A \times B)/C \times M$ where
A: mols of the organometallic compound catalyst
B: Valence of the organometallic compound catalyst
C: Valence of the polyhydric alcohol
M: molecular weight of the polyhydric alcohol The treatment of the esterification reaction product containing the catalyst with the polyhydric alcohol, is conducted in such a manner that after the esterification reaction, a predetermined amount of the polyhydric alcohol is added to the reaction product containing the catalyst obtained by distilling off any excess alcohol, then the mixture is uniformly mixed and then maintained at a temperature lower than the above esterification temperature (at least 180° C.), preferably at a temperature of at least 140° C. and lower than 180° C., for at least 5 minutes, and then filtered at a temperature of not higher than 140° C. By such treatment, the reaction product of the organometallic compound catalyst with the polyhydric alcohol is removed as solid, to obtain a high quality ester useful as a plasticizer. Further, by incorporating an adsorbing agent for by-product, such as magnesium oxide or active carbon at the time of treating with the above polyhydric alcohol, an ester of a still higher quality is obtainable.

Now, the present invention will be described in further detail with reference to Examples and Comparative Examples. However, it should be understood that the present invention is by no means restricted to such specific Examples.

EXAMPLE 1

74 g (0.5 mol) of phthalic anhydride and 163 g (1.25 mols) of 2-ethylhexanol were mixed, and 0.36 g (0.001 mol) of tetraisopropyl titanate was added thereto. The mixture was heated under stirring, and a dehydration esterification reaction was conducted at a temperature of from 190° to 215° C. for 3 hours. After completion of the reaction, excess 2-ethylhexanol was distilled off under a reduced pressure of from 5 to 40 mmHg.

To the esterification reaction product, 0.13 g (0.001 mol) of pentaerythritol was added, and the mixture was stirred at 180° C. for 20 minutes and then cooled to 120° C. Then, 0.2 g of magnesium oxide and 0.1 g of active carbon were added thereto, followed by filtration at the same temperature to remove the solid substance to obtain dioctyl phthalate (DOP). The time required for the purification treatment step subsequent to the addition of pentaerythritol was 1.5 hours, and the amount of water used was 0. The acid value, the volume resistivity (liquid VR) according to JIS K6751, the color hue and the titanium content of the dioctyl phthalate thus obtained, were as follows, and they had values equal or superior to DOP obtained by the conventional methods.

Acid value: 0.01 mgKOH/g
Liquid VR: $15 \times 10^{11} \Omega cm$
Color hue (APHA): 10
Ti content: At most 5 ppm

EXAMPLE 2

In the same manner as in Example 1, phthalic anhydride and 2-ethylhexanol were subjected to a dehydration esterification reaction using tetraisopropyl titanate as the catalyst. After completion of the reaction, excess 2-ethylhexanol was distilled off to obtain a reaction product, to which 0.13 g (0.001 mol) of pentaerythritol was added. The mixture was stirred at 160° C. for 20 minutes, and the subsequent treatment was conducted in the same manner as in Example 1 to obtain DOP. The time required for the purification treatment step subsequent to the addition of pentaerythritol was 1.5 hours, and the amount of water used was 0. The acid value, the liquid VR, the color hue and the titanium content of DOP thus obtained, were as follows:

Acid value: 0.01 mgKOH/g
Liquid VR: $14 \times 10^{11} \Omega cm$
Color hue (APHA): 10
Ti content: Not more than 5 ppm

EXAMPLE 3

In the same manner as in Example 1, phthalic anhydride and 2-ethylhexanol were subjected to an esterification reaction using tetraisopropyl titanate as the catalyst. After completion of the reaction, excess 2-ethylhexanol was distilled off to obtain a reaction product, to which 0.3 g (0.0025 mol) of pentaerythritol was added. The mixture was stirred at 180° C. for 20 minutes, and the subsequent treatment was conducted in the same manner as in Example 1 to obtain DOP. The time required for the purification treatment step subsequent to the addition of pentaerythritol was 1.5 hours, and the amount of water used was 0. The acid value, the liquid VR, the color hue and the titanium content of DOP thus obtained, were as follows:

Acid value: 0.01 mgKOH/g
Liquid VR: $13 \times 10^{11} \Omega cm$
Color hue (APHA): 15
Ti content: Not more than 5 ppm

COMPARATIVE EXAMPLE 1

In the same manner as in Example 1, phthalic anhydride and 2-ethylhexanol were subjected to an esterification reaction using tetraisopropyl titanate as a catalyst. After completion of the reaction, excess 2-ethylhexanol was distilled off to obtain a reaction product. Then, 50% by weight of water and 0.5% by weight of sodium carbonate were added to the reaction product, and the mixture was stirred at 100° C. and then subjected to liquid separation. The aqueous phase was removed, and the organic phase was washed twice using the same amount of water. Then, the temperature was raised and steam stripping was conducted at 140° C., followed by filtration at 110° C. to remove solid substances to obtain DOP. The time required for the purification treatment step subsequent to the addition of water and sodium carbonate, was 5 hours, and the amount of water used was 600 ml. The acid value, the liquid VR, the color hue and the titanium content of DOP obtained, were as follows:

Acid value: 0.01 mgKOH/g
Liquid VR: $13 \times 10^{11} \Omega cm$
Color hue (APHA): 15
Ti content: Not more than 5 ppm

EXAMPLE 4

In the same manner as in Example 1, phthalic anhydride and 2-ethylhexanol were subjected to an esterification reaction using tetraisopropyl titanate as a catalyst. After completion of the reaction, excess 2-ethylhexanol was distilled off to obtain a reaction product, to which 0.17 g (0.001 mol) of dipentaerythritol was added. The mixture was stirred at 180° C. for 20 minutes, and the subsequent treatment was conducted in the same manner as in Example 1 to obtain DOP.

The time required for the purification treatment step subsequent to the addition of dipentaerythritol was 1.5 hours, and the amount of water used was 0. The acid value, the liquid VR, the color hue and the titanium content of DOP thus obtained, were as follows:

Acid value: 0.01 mgKOH/g
Liquid VR: $14 \times 10^{11} \Omega cm$
Color hue (APHA): 10

Ti content: Not more than 5 ppm

It is evident from the above Examples and Comparative Examples that when the esterification reaction product is treated with the polyhydric alcohol in accordance with the method of the present invention, the catalyst contained in the reaction product can readily be removed, whereby the ester can be obtained economically advantageously without requiring such a long time as required for the purification treatment in the conventional wet method and with less consumption of water for washing or heat energy. Yet, the quality of the ester thereby obtained is excellent and equal or superior to that attainable by the conventional methods.

What is claimed is:

1. A method for producing an ester, which comprises reacting an organic acid or its anhydride with an alcohol in the presence of a catalyst of an organometallic compound, wherein an esterification reaction product containing the catalyst, is treated with a polyhydric alcohol at a temperature of at least 140° C. and less than 180° C. for at least five minutes.

2. The method according to claim 1, wherein the catalyst of an organometallic compound is a tetraalkyl titanate showing catalytic activities at a temperature of at least 180° C.

3. The method according to claim 1, wherein the polyhydric alcohol used for the treatment, is trimethylolpropane, trimethylolbutane, pentaerythritol or dipentaerythritol.

4. The method according to claim 1, wherein the ester is di-2-ethylhexyl phthalate.

5. The method according to claim 1, wherein the treatment of the esterification reaction product containing the catalyst with the polyhydric alcohol is followed by filtration at a temperature of not higher than 140° C.

* * * * *